United States Patent
Boyle et al.

(10) Patent No.: US 6,394,978 B1
(45) Date of Patent: May 28, 2002

(54) INTERVENTIONAL PROCEDURE EXPANDABLE BALLOON EXPANSION ENABLING SYSTEM AND METHOD

(75) Inventors: William Joseph Boyle, Fallbrook; Andy Edward Denison, Temecula; Benjamin Curtis Huter, Murrieta; Scott Jason Huter, Temecula, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 121 days.

(21) Appl. No.: 09/634,217

(22) Filed: Aug. 9, 2000

(51) Int. Cl.[7] .............................................. A61M 29/00
(52) U.S. Cl. ................................. 604/103.06; 604/104
(58) Field of Search ...................... 604/103.06, 103.07, 604/103.08, 103.09, 103.1, 104, 105, 107

(56) References Cited

U.S. PATENT DOCUMENTS

| | | | |
|---|---|---|---|
| 4,723,549 A | 2/1988 | Wholey et al. | |
| 4,997,435 A | 3/1991 | Demeter | |
| 5,100,425 A | 3/1992 | Fischell et al. | |
| 5,158,548 A | 10/1992 | Lau et al. | |
| 5,242,399 A | * 9/1993 | Lau et al. | 604/104 |
| 5,437,632 A | 8/1995 | Engleson | |
| 5,573,508 A | * 11/1996 | Thornton | 604/102.02 |
| 5,814,064 A | 9/1998 | Daniel et al. | |
| 5,827,324 A | 10/1998 | Cassell et al. | |
| 5,846,251 A | 12/1998 | Hart | |
| 5,891,154 A | * 4/1999 | Loeffler | 606/194 |
| 5,911,734 A | 6/1999 | Tsugita et al. | |
| 5,980,555 A | 11/1999 | Barbut et al. | |
| 5,989,281 A | 11/1999 | Barbut et al. | |
| 6,029,671 A | * 2/2000 | Stevens et al. | 128/898 |
| 6,210,312 B1 | * 4/2001 | Nagy | 600/3 |
| 6,217,586 B1 | * 4/2001 | Mackenzie | 606/108 |
| 6,306,151 B1 | * 10/2001 | Lary | 604/96.01 |
| 6,309,412 B1 | * 10/2001 | Lau et al. | 623/1.11 |
| 6,325,814 B1 | * 12/2001 | Euteneuer et al. | 606/108 |

* cited by examiner

Primary Examiner—Teresa Walberg
Assistant Examiner—Vinod D Patel
(74) Attorney, Agent, or Firm—Fulwider Patton Lee & Utecht, LLP (57) ABSTRACT

A system used in a blood vessel when an interventional procedure is being performed in a stenosed or occluded region, which is capable of enabling an expandable balloon to be expandable in a blood vessel, from unexpanded condition thereof wherein portions of the expandable balloon are in contact, while preventing the unexpanded in-contact portions of the balloon from sticking together during expansion and deployment of the expandable balloon. The system includes a catheter which is positionable in a blood vessel at the interventional procedure site., The system further includes an expandable member such as an expandable balloon, which is expandable and which may be deployed in the blood vessel at the interventional procedure site, which includes portions thereof which are in contact in the unexpanded condition, wherein the expandable balloon is capable of expanding while preventing the unexpanded in-contact portions thereof from sticking together during expansion and deployment thereof.

26 Claims, 5 Drawing Sheets

INTERVENTIONAL PROCEDURE EXPANDABLE BALLOON EXPANSION ENABLING SYSTEM AND METHOD

BACKGROUND OF THE INVENTION

The present invention relates generally to a system which can be used when an interventional procedure is being performed in a stenosed or occluded region of a blood vessel, to enable an expandable member to be substantially-freely expandable for filtering of the blood in the blood vessel or for occluding the blood vessel during the procedure. The system of the present invention is particularly useful when performing balloon angioplasty, stenting procedures, laser angioplasty or atherectomy in critical vessels, such as the carotid arteries.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter is usually used to capture the shaved plaque or thrombus from the blood stream during this procedure.

In another widely practiced procedure, the stenosis can be treated by placing a device known as a stent into the stenosed region to hold open and sometimes expand the segment of blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

Prior art stents typically fall into two general categories of construction. The first type of stent is expandable upon application of a controlled force, often through the inflation of an expandable member such as an expandable balloon in a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanum (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not fully vaporized and enter the bloodstream. Likewise, not all of the emboli created during an atherectomy procedure may be drawn into the vacuum catheter and, as a result, the remaining emboli may enter the bloodstream as well.

When any of the above-described procedures are performed in the cerebral arteries, the release of emboli into the circulatory system can be extremely dangerous and sometimes fatal to the patient. Debris that is carried by the bloodstream to distal vessels supplying the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, often making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Further techniques which have had success include occluding of the blood vessel with an occluding balloon and perfusing the blood through a perfusion catheter past the occlusion, and the placement of a balloon filter or trap downstream from the treatment site to capture embolic debris before it reaches the smaller blood vessels downstream. However, there have been problems associated with filtering and occluding systems, particularly during the expansion of the occluding balloon and balloon filter within the blood vessel. The portions of the balloon wall which are in contact in the unexpanded condition of the balloon may stick together, inhibiting the expansion and deployment of the balloon.

The above problems my arise from the expansion characteristics of the wall of the expandable balloon. The thickness of the wall of the expandable balloon may be substantially uniform, whereby the unexpanded in-contact portions of the balloon wall may tend to stick together and prevent deployment during expansion thereof, interfering the filtering of blood in the blood vessel or preventing the balloon from fully deploying within the vessel.

What has been needed is a reliable system and method for treating stenosis in blood vessels which enables the wall of the expandable balloon to be expandable, preventing portions thereof from sticking together during deployment and enabling full deployment of the balloon member in the area of treatment. The system and method should be relatively easy for a physician to use. Moreover, such a system should be relatively easy to deploy and remove from the patient's vasculature. The inventions disclosed herein satisfy all of these and other needs.

SUMMARY OF INVENTION

The present invention provides a system and method for enabling an expandable balloon to be expandable in a blood vessel during the performance of a therapeutic interventional procedure, such as a balloon angioplasty or stenting procedure, while preventing unexpanded in-contact portions thereof from sticking together during expansion and deployment of the expandable balloon. The present invention is particularly useful while performing an interventional procedure in vital arteries, such as the carotid arteries, in which critical downstream blood vessels can become blocked with embolic debris, including the main blood vessels leading to the brain or other vital organs. As a result, the present invention provides the physician with a higher degree of confidence that the expandable balloon will expand for occluding the blood vessel or for filtering the blood in the blood vessel thereby, and that the unexpanded in-contact portions of the expandable balloon will not stick together and inhibit deployment during expansion thereof.

The present invention enables an interventional procedure to be performed in a blood vessel at an interventional procedure site, such that the expandable balloon will expand and deploy for occluding or filtering thereby.

In the present invention, the system includes a catheter for positioning in a blood vessel at an interventional procedure site, an expandable member located in a distal end portion of the catheter for expanding and deploying in the blood vessel at the interventional procedure site, which includes a wall having an inner surface that includes portions thereof which are in contact in unexpanded condition, and an element for enabling the expandable balloon to be expandable.

In an embodiment of the present invention, the system includes a catheter, including an elongated shaft which includes a distal end portion adapted to be positioned in a blood vessel at an interventional procedure site. An expandable member, such as an expandable balloon, is adapted to be located in the distal end portion of the catheter shaft, and to be expanded and deployed in the blood vessel relative to the interventional procedure site, which expandable balloon includes a wall which includes a portion adapted to be fixed to the catheter shaft and a portion adapted to be expandable. The wall is adapted to be relatively stiff proximate the fixed portion thereof, and relatively flexible proximate the expandable portion thereof. The expandable balloon is in fluid communication with an inflation lumen. Upon inflation with a suitable fluid, the expandable balloon is expandable so as to be deployed within the blood vessel at the interventional procedure site, for occluding the blood vessel or for filtering the blood in the blood vessel. The expandable balloon enables deployment and prevents sticking together thereof upon expansion of the unexpanded in-contact portions.

In a particular embodiment of the present invention, the thickness of the wall of the expandable member is adapted to be substantially variable from the fixed portion to the expandable portion thereof, with the substantially variable thickness of the wall adapted to be substantially thick towards the fixed portion thereof, and substantially thin towards the expandable portion thereof. The substantially variable thickness of the expandable balloon wall enables the expandable balloon to be expandable while exhibiting sticking together of portions thereof.

In another particular embodiment of the present invention, the expandable balloon further includes an enlarged portion located remote from the fixed portion thereof, for enhancing the ability of the expandable balloon to expand and deploy while preventing portions thereof from sticking together.

Other features and advantages of the present invention will become more apparent from the following detailed description of the preferred embodiments of the invention, when taken in conjunction with the accompanying exemplary drawings.

DETAILED DESCRIPTION OF THE PREFERRED EMBODIMENTS

The present invention is directed to an improved system and method for efficiently and effectively enabling an interventional procedure to be performed in a blood vessel at an interventional procedure site so that an expandable member is expandable in the blood vessel, from unexpanded condition thereof wherein portions of the expandable member are in contact, while inhibiting the unexpanded in-contact portions of the expandable member from sticking together during the expansion and deployment of the expandable member. The preferred embodiments of the improved system and method are illustrated and described herein by way of example only and not by way of limitation. While the present invention is described in detail as applied to the carotid arteries of the patient, and the disclosed interventional procedure is directed to a stenting procedure, those skilled in the art will appreciate that it can also be used in other body lumens as well, such as the coronary arteries, renal arteries, saphenous veins and other peripheral arteries. Additionally, the present invention can be utilized when performing any one of a number of interventional procedures, such as balloon angioplasty, laser angioplasty or atherectomy.

Figure 1:
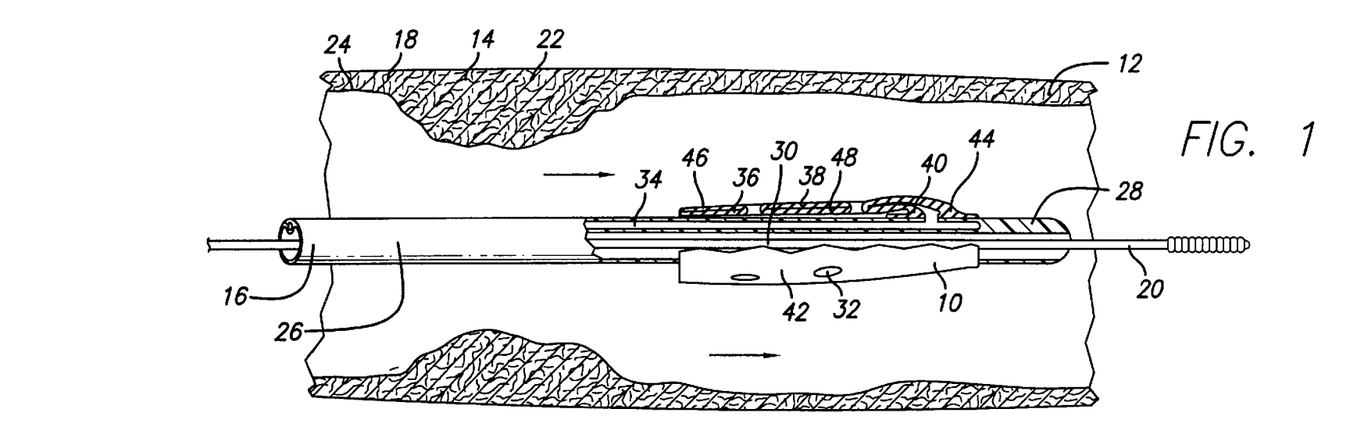
FIG. 1 is an elevational view, partially in section, depicting the system of the present invention disposed within the internal carotid artery of a patient, including a catheter, and a first version of a first embodiment of an expandable member, for filtering and capturing embolic material, in unexpanded condition.
Figure 2:
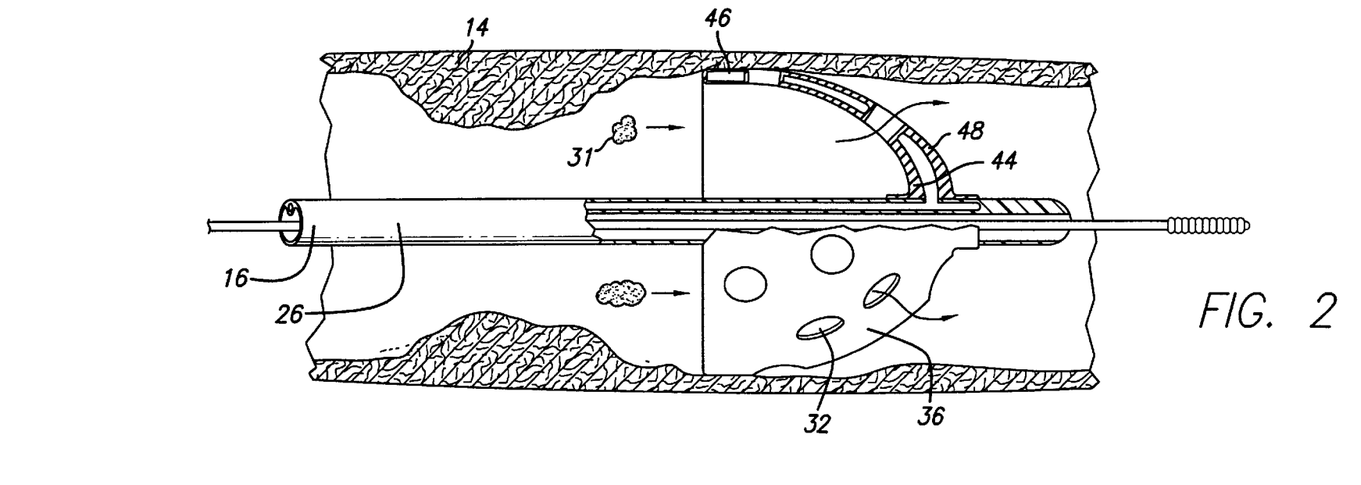
FIG. 2 is an elevational view, partially in section, similar to that shown in FIG. 1, wherein the expandable member is in expanded condition.

Referring now to the drawings, wherein like reference numerals denote like or corresponding parts throughout the drawing figures, and particularly to FIGS. 1–8, a system 10 is provided for enabling an interventional procedure to be performed in a blood vessel 12 at an area of treatment 14. The system 10 includes a catheter 16 adapted to enable the interventional procedure to be performed. As shown in FIG. 2, the system 10 may be positioned on the catheter 16, and may be placed within the carotid artery 18 or other blood vessel of the patient on the catheter 16 and guided into position by riding over or being fixed to a guide wire 20. The carotid artery 18 may have the area of treatment 14, which may comprise the interventional procedure site, wherein atherosclerotic plaque 22 may have built up against the inside wall 24 which decreases the diameter of the carotid artery 18. As a result, blood flow may be diminished through this area. The catheter 16 may include an elongated shaft 26 having a distal end 28.

Figure 7:
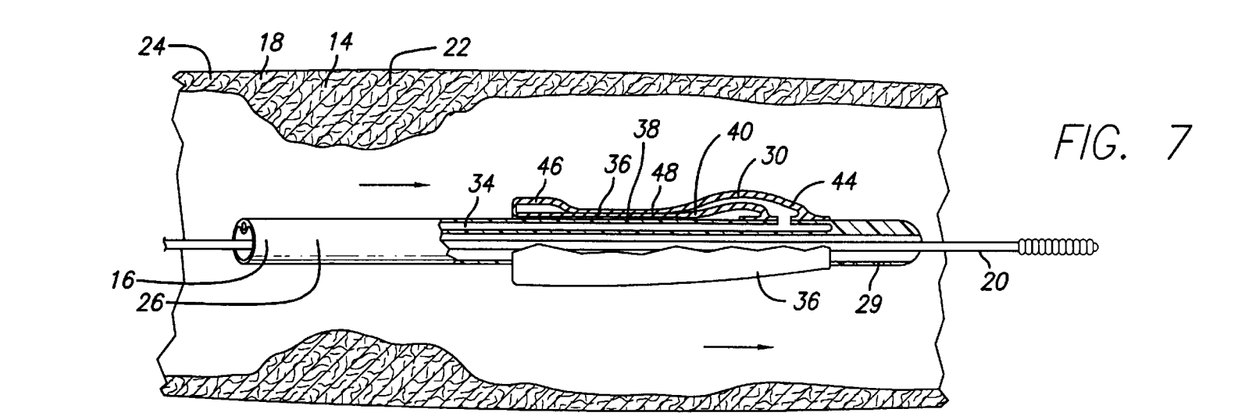
FIG. 7 is an elevational view, partially in section, depicting the system of the present invention disposed within the internal carotid artery of a patient, including a catheter and a first version of a second embodiment of an expandable member, for occluding the blood vessel, in unexpanded condition.
Figure 8:
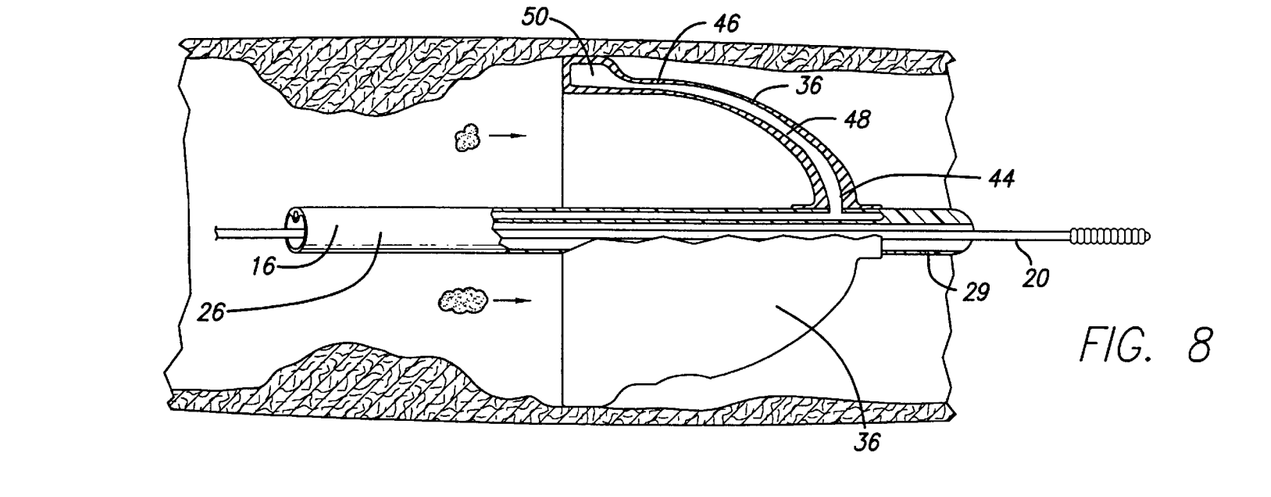
FIG. 8 is an elevational view, partially in section, similar to that shown in FIG. 7, including a second version of the second embodiment of an expandable member in expanded condition.

An expandable member 30 may be positioned proximate the distal end 28 of the elongated shaft 26 of the catheter 16, and may be adapted to be expanded and deployed distal to the interventional procedure site 14. In the embodiment of the system 10 as shown in FIGS. 1–6, the expandable member 30 is adapted to filter the blood in the blood vessel 12 upon expansion of the expandable member 30, so as to pass blood therethrough and capture embolic material 31 which may be released into the blood in the blood vessel 12 during the interventional procedure. In such embodiment, the expandable member 30 may include a plurality of openings 32 therein, adapted to enable blood to flow therethrough and to prevent emboli 31 from passing therethrough. In the embodiment of the system 10 as shown in FIGS. 7–8, the expandable member 30 is adapted to occlude the blood vessel 12 upon expansion of the expandable member 30, to prevent blood flow past the expandable member 30, and the catheter 16 is adapted to enable blood to flow therethrough, with blood flow enabled past the occlusion through perfusion openings 29 in the catheter 16. In such embodiment, the expandable member 30 is a substantially solid member.

For expanding and contracting the expandable member 30, an inflation lumen 34 may extend to the distal end 28 of the elongated catheter shaft 26. The inflation lumen 34 may receive and remove fluid, such as saline or other inflation fluid. As can be seen in FIG. 2, the expandable member 30 may be expanded in a direction generally transverse to the axial dimension thereof so as to expand and deploy the expandable member 30 to make full contact with and compress the plaque 22 in the walls 24 of the carotid artery 18.

The expandable member 30 may comprise an expandable balloon. The expandable balloon 30 may for example be generally conical-shaped. It may include a wall 36, which includes an inner surface 38, including portions 40 and 42 which may be in contact in unexpanded condition of the expandable balloon 30. The expandable balloon 30 may further include a portion 44 adapted to be fixed, and a portion 46 adapted to be expandable. The expandable portion 46 of the wall 36 may be located remote from the fixed portion 38 thereof.

The expandable balloon 30 may be adapted to enable expansion of the unexpanded in-contact portions 40 and 42, to be expandable in the blood vessel 12 distal to the interventional procedure site 14, so as to prevent such portions 40 and 42 from sticking together upon expansion of the expandable balloon 30.

Figure 3:
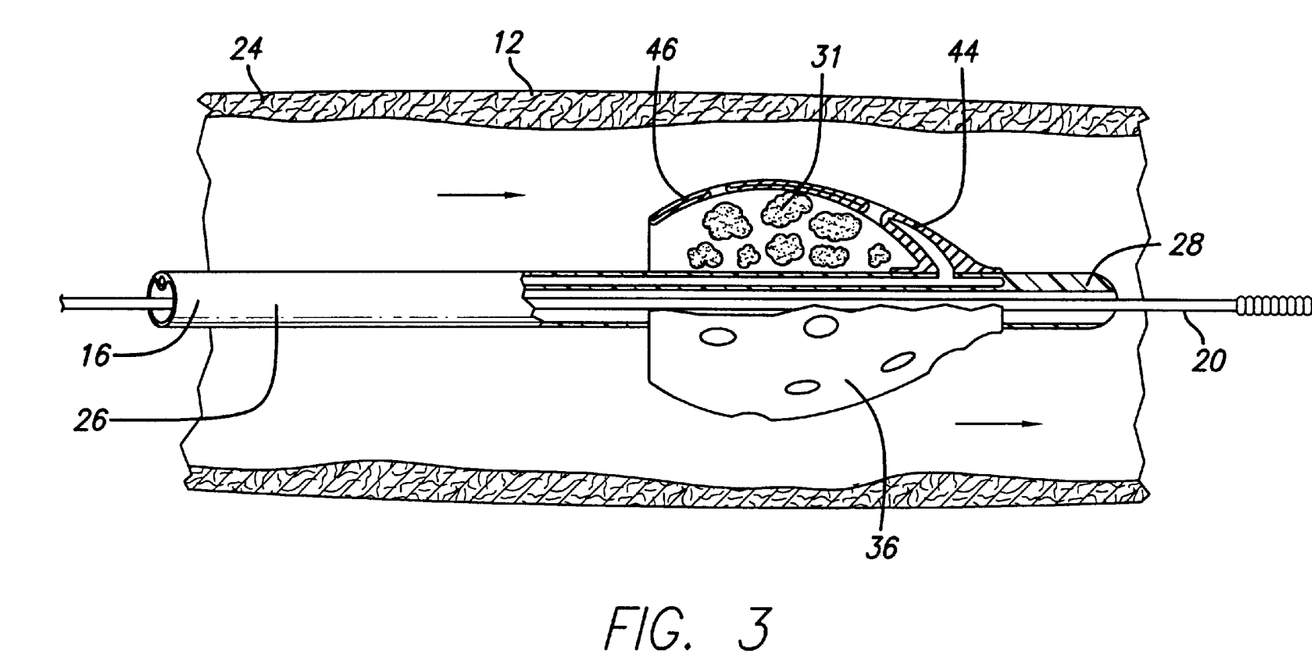
FIG. 3 is an elevational view, partially in section, similar to that shown in FIG. 2, wherein the expandable member is in collapsed condition.

In the embodiment of the invention for capturing embolic material as shown in FIGS. 1–6, in a version shown in FIGS. 1–3, the expandable balloon 30 may further include an element 48 for enabling the unexpanded in-contact portions 40 and 42 of the inner surface 38 of the wall 36 to be expandable in the blood vessel 12 distal to the interventional procedure site 14 upon expansion of the expandable balloon 30. The expansion enabling element 48 may comprise the thickness of the wall 36 being substantially variable from the fixed portion 44 to the expandable portion 46. The substantially-variable thickness of the wall 36 may be substantially incrementally variable, which may comprise a stepped incremental variation. It may be thicker, and may be substantially thick, towards the fixed portion 44 thereof, so as to be relatively stiff at such portions. The substantially variable thickness of the wall 36 may be substantially thin towards the expandable portion 46 thereof, so as to be relatively flexible at such portions. It may be adapted to vary for example in a range of about 0.003 inches to 0.007 inches at a location proximate the fixed portion 44 to a range of about 0.001 inches to 0.0015 inches at a location spaced from the fixed portion 44.

Figure 4:
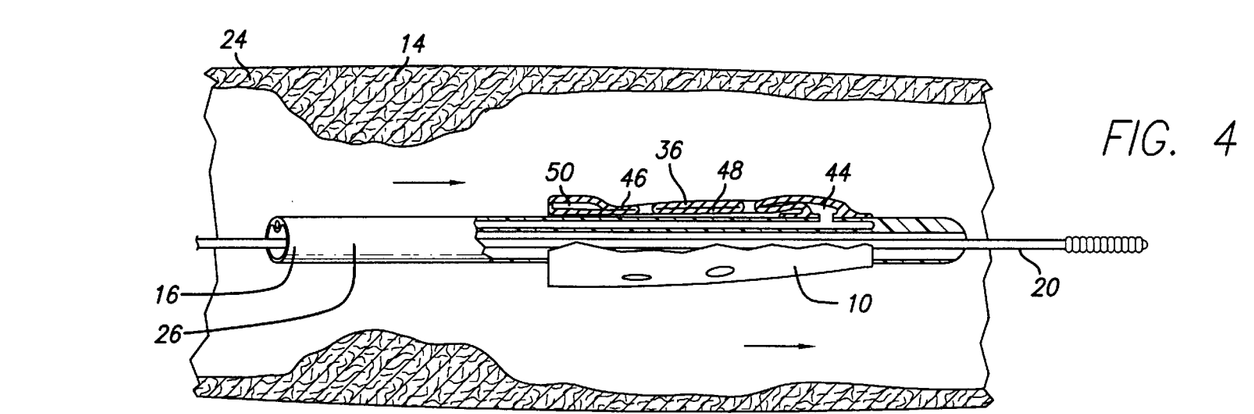
FIG. 4 is an elevational view, partially in section, depicting the system of the present invention disposed within the internal carotid artery of a patient, including a catheter, and a second version of the first embodiment of an expandable member in unexpanded condition.
Figure 5:
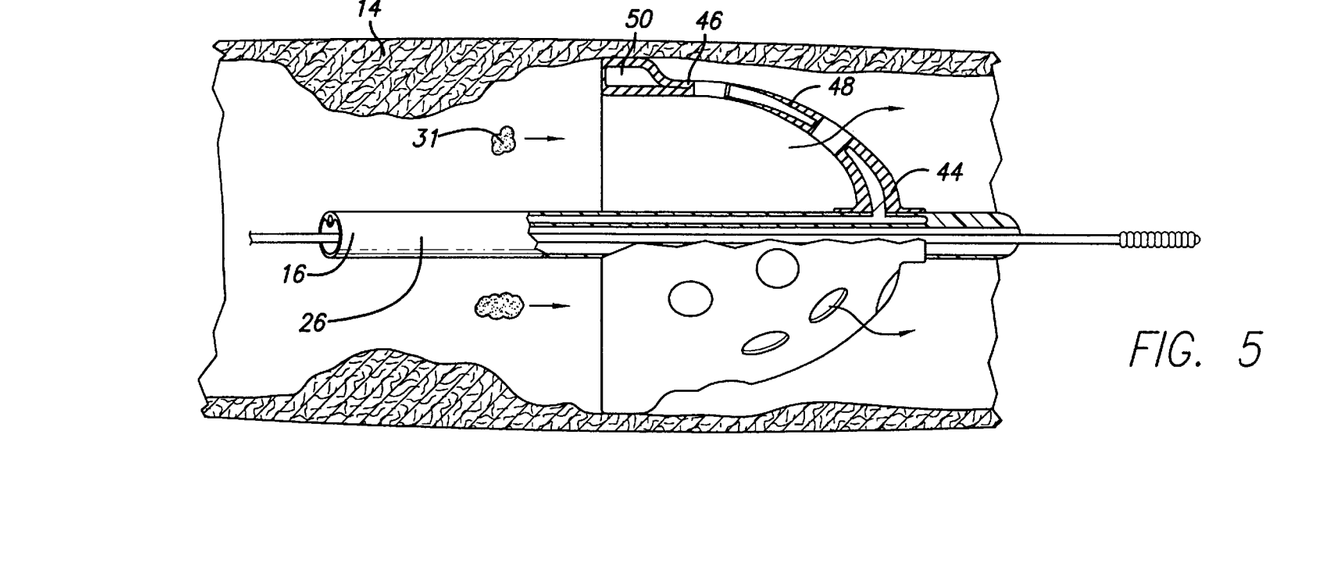
FIG. 5 is an elevational view, partially in section, similar to that shown in FIG. 4, wherein the expandable member is in expanded condition.
Figure 6:
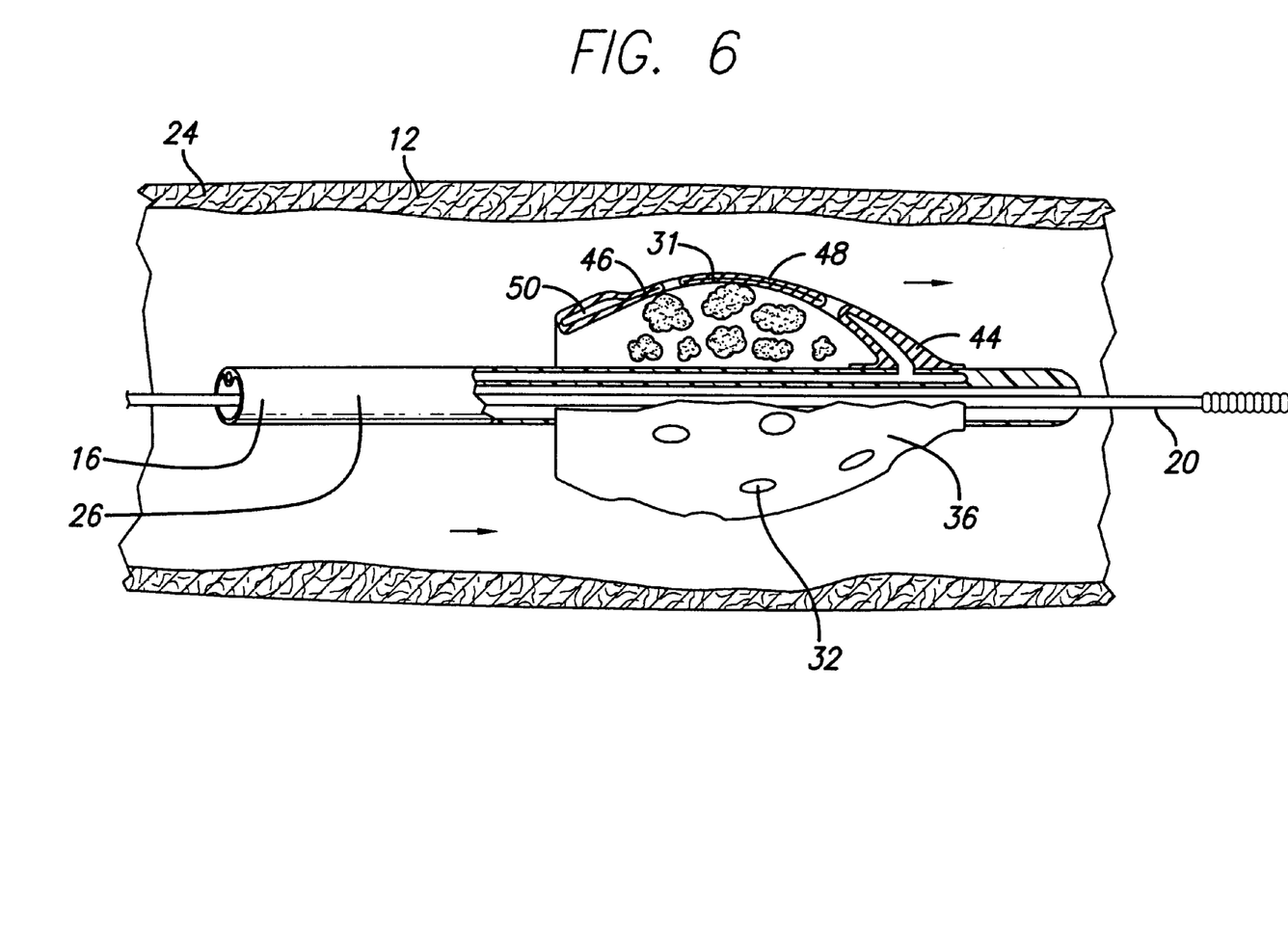
FIG. 6 is an elevational view, partially in section, similar to that shown in FIG. 5, with the expandable member in collapsed condition.

In another version of the embolic-material capturing embodiment of the invention as shown in FIGS. 4–6, the substantially variable thickness wall 36 of the expandable balloon 30 may further include the enlarged portion 50 which may be located remote from the fixed portion 44. The thickness of the enlarged portion 50 may vary for example in a range of about 0.003 inches to 0.007 inches.

In the embodiment of the invention for occluding the blood vessel 12 as shown in FIGS. 7–8, in a version shown in FIG. 7, the expandable balloon 30 includes the expansion enabling element 48 of the substantially-variable thickness of the wall 36 as in the above embolic-material capturing embodiment shown in FIGS. 1–3. In another version of the blood-vessel occluding embodiment of the invention as shown in FIG. 8, the substantially variable thickness wall 36 of the expandable balloon 30 may further include the enlarged portion 50 which may be located remote from the fixed portion 44 as in the above embolic-material capturing embodiment shown in FIGS. 4–6.

In use, as illustrated in FIGS. 1–8, the system 10 may be positioned in the patient's vasculature utilizing any one of a number of different methods. In one preferred method of positioning, the catheter 16 may be placed in the blood vessel 12 by utilizing the guidewire 20 which is inserted into the patient's vasculature and manipulated by the physician to the area of treatment 14. Thereafter, once the guidewire 20 is in place, the catheter 16 may be maneuvered over the guidewire 20 (via a central lumen) using well-known over-the-wire techniques to place the catheter 16 at a location proximal to the area of treatment 14. Once the catheter 16 is in position in the blood vessel 12 with the expandable balloon 30 at the treatment area 14, the expandable balloon 30 of the catheter 16 may be deployed at the treatment area 14 by inflating the expandable member 32 through the lumen 34. The inflation of the expandable balloon 30 may be initiated at a proximal end of the elongated shaft 26 of the catheter 16 by utilizing a multi-arm adapter which may be attached to an inflation pump or syringe to expand the expandable balloon 30.

Upon inflation, the expandable balloon 30 may expand into position at the treatment area 14. The expansion-enabling element 48 of the expandable balloon 30 provides relative stiffness of the expandable balloon wall 24 proximate the fixed portion 44 thereof, and relative flexibility of the expandable balloon wall 24 proximate the expandable portion 46 thereof. This enables the expandable balloon 30 to expand, so as to enable the expandable balloon 30 to be expanded and deployed in the blood vessel 12 distal to the treatment area 14, without the unexpanded in-contact portions 40 and 42 sticking to themselves. After the expandable balloon 30 is deployed in the treatment area 18, the expandable balloon 30 may be deflated by removing the fluid therein through the lumen 34 to collapse the expandable balloon 30, and the catheter 16 may be withdrawn. The deflation of the expandable balloon 30 may be initiated at the proximal end of the elongated shaft 26 of the catheter 16, utilizing the multi-arm adapter which may be attached to the inflation pump or syringe.

In the embodiments of the invention illustrated in FIGS. 1–8, an interventional device, such as the catheter 16, including the expandable balloon 30 may be positioned in the patient's vasculature in the area of treatment 18 utilizing the elongated shaft 26 of the catheter 16 and the guide wire 20, using the well-known over-the-wire techniques. Upon positioning the expandable balloon 30 at the treatment area 18, the expandable balloon 30 may be expanded in a direction generally transverse to the axial dimension thereof by receiving fluid through the lumen 34, which expands the expandable balloon 30. The expansion enabling element 48 of the wall 36 enables the unexpanded in-contact portions 40 and 42 to be expandable without sticking together. As seen in the version of the embodiment of the invention in FIGS. 1–3, the expansion enabling element 48, which comprises the substantially variable thickness from the thicker fixed portion 44 to the thinner expandable portion 46, enables effective and efficient expansion of the expandable balloon 30 for filtering of the blood in the blood vessel 12. As seen in the version of the embodiment in FIGS. 4–6, the expansion enabling element 48, which also comprises the enlarged portion 50 located remote from the fixed portion 44, enhances the expansion of the expandable balloon 30 for effective filtering of the blood in the blood vessel 12. As seen in the version of the embodiment of the invention in FIG. 7, the expansion enabling element 48, which comprises the substantially variable thickness from the thicker fixed portion 44 to the thinner expanded portion 46, enables efficient expansion of the expandable balloon 30 for occluding the blood vessel 12. As seen in the version of the embodiment in FIG. 8, the expansion enabling element 48, which also comprises the enlarged portion 50 located remote from the fixed portion 44, enhances the expansion of the expandable balloon 30 for effective occlusion of the blood vessel 12.

The process of forming the expandable balloon 30 may comprise, for example, dip molding, wherein the expandable balloon 30 is formed on a mandrel by dipping it in a polymer and peeling it off the mandrel. In the filtering embodiment as shown in FIGS. 1–6, the opening 32 may be formed, for example, by a laser cutting holes in the expandable balloon 30 of a size, for example, of 130 microns.

It should be appreciated that the particular embodiments of the expandable member 30 are capable of being positioned in the blood vessel 14. However, other forms of the expandable member 30 may be utilized with the present invention without departing from the spirit and scope of the invention. For example, the expandable member 30 may further be comprised of other forms of material. Additionally, while the expandable member 30 is shown as in various shapes in the embodiments herein, it can be formed in any one of a number of different shapes depending upon the construction desired.

The catheter assembly 16 of the present invention may be formed of conventional materials of construction. The catheter shaft 26 can be made out of relatively inelastic materials such as polyethylene, polyvinyl chloride, polyesters and composite materials. The various components may be joined by suitable adhesives based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed.

In view of the foregoing, it is apparent that the system and method of the present invention enhances substantially the effectiveness of performing interventional procedures by substantially retaining the unexpanded axial dimension of an expandable interventional instrument upon expansion thereof to accurately and effectively pin and compress plaque at the interventional procedure site. Further modifications and improvements may additionally be made to the system and method disclosed herein without the departing from the scope of the invention. Accordingly, it is not intended that the invention be limited, except as by the appended claims.

What is claimed:

1. A system for enabling an interventional procedure to be performed in a blood vessel at an interventional procedure site, comprising:

a catheter, including an elongated shaft which includes a distal end portion adapted to be positioned in a blood vessel distal to an interventional procedure site; and an expandable member, adapted to be located in the distal end portion of the catheter shaft, and to be expanded and deployed in the blood vessel distal to the interventional procedure site, including a wall having an inner surface including portions thereof which are adapted to be substantially in contact in unexpanded condition, and including means for enabling expansion of the unexpanded substantially in contact portions of the inner surface of the wall to be expandable in the blood vessel distal to the interventional procedure site upon expansion of the expandable member, wherein the expandable member wall includes a portion adapted to be fixed and a portion adapted to be expandable, and the expansion enabling means comprise the thickness of the wall being adapted to be substantially variable from the fixed portion to the expandable portion.

2. The system of claim 1, wherein the expansion enabling means are further adapted to enable the expandable member wall to be relatively stiff proximate the fixed portion thereof and relatively flexible proximate the expandable portion thereof.

3. The system of claim 2, wherein the expandable portion of the wall is adapted to be located remote from the fixed portion thereof.

4. The system of claim 2, wherein the wall is adapted to include an enlarged portion which is located remote from the fixed portion thereof.

5. The system of claim 1, wherein the substantially variable thickness of the wall is adapted to be substantially incrementally variable.

6. The system of claim 1, wherein the substantially variable thickness of the wall is adapted to be thicker towards the fixed portion thereof.

7. The system of claim 1, wherein the substantially variable thickness of the wall is adapted to be substantially thick towards the fixed portion thereof.

8. The system of claim 1, wherein the substantially variable thickness of the wall is adapted to be substantially thin towards the expandable portion thereof.

9. The system of claim 1, wherein the substantially variable thickness of the wall is adapted to vary from approximately 0.007 inches at a location proximate the fixed portion to approximately 0.0015 inches at a location spaced from the fixed portion.

10. The system of claim 1, wherein the substantially variable thickness of the wall is adapted to vary from approximately 0.003 inches at a location spaced from the expandable portion to approximately 0.0010 at a location proximate the expandable portion.

11. The system of claim 1, wherein the expandable member comprises an expandable balloon.

12. The system of claim 1, wherein the expandable member is adapted to filter the blood in the blood vessel therethrough upon expansion thereof, so as to pass blood therethrough and capture embolic material which may be released into the blood in the blood vessel during the interventional procedure.

13. The system of claim 12, wherein the wall has a plurality of openings therein, adapted to enable blood to flow therethrough in the blood vessel and to prevent emboli from passing therethrough.

14. The system of claim 13, wherein the thickness of the enlarged portion is approximately 0.007 inches.

15. The system of claim 1, wherein the expandable member is adapted to occlude the blood vessel upon expansion thereof, so as to prevent blood flow past the expandable member, and wherein the catheter is adapted to enable blood to flow past the occlusion.

16. The system of claim 1, wherein the expandable member is adapted to be generally parabolic-shaped.

17. A system for enabling an interventional procedure to be performed in a blood vessel at an interventional procedure site, comprising:

a catheter, including an elongated shaft which includes a distal end portion adapted to be positioned in a blood vessel distal to an interventional procedure site; and means for expanding and deploying in the blood vessel distal to the interventional procedure site, adapted to be located in the distal end portion of the catheter shaft, including a wall having a portion adapted to be fixed and a portion adapted to be expandable, and which includes an inner surface including portions thereof which are adapted to be substantially in contact in unexpanded condition, and including means for enabling the unexpanded substantially in-contact portions of the inner surface of the wall to be expandable in the blood vessel distal to the interventional procedure site upon expansion of the expanding means, wherein the expandable member wall includes a portion adapted to be fixed and a portion adapted to be expandable, and the expansion enabling means comprise the thickness of the wall being adapted to be substantially variable from the fixed portion to the expandable portion, and wherein the substantially variable thickness of the wall is adapted to be substantially incrementally variable.

18. The system of claim 17, wherein the substantially variable thickness of the wall is adapted to be thicker towards the fixed portion thereof.

19. The system of claim 17, wherein the substantially variable thickness of the wall is adapted to be substantially thick towards the fixed portion thereof.

20. The system of claim 17, wherein the substantially variable thickness of the wall is adapted to be substantially thin towards the expandable portion thereof.

21. A method of enabling an interventional procedure to be performed in a blood vessel at an interventional procedure site, in a system which comprises a catheter, including an elongated shaft which includes a distal end portion adapted to be positioned in a blood vessel distal to an interventional procedure site, and an expandable member, adapted to be located in the distal end portion of the catheter shaft, and to be expanded and deployed in the blood vessel distal to the interventional procedure site, including a wall having an inner surface including portions thereof which are adapted to be substantially in contact in unexpanded condition, and including means for enabling expansion of the unexpanded substantially in-contact portions of the inner surface of the wall to be expandable in the blood vessel distal to the interventional procedure site upon expansion of the expandable member, wherein the expandable member wall includes a portion adapted to be fixed and a portion adapted to be expandable, and the expansion enabling means comprise the thickness of the wall being adapted to be substantially variable from the fixed portion to the expandable portion, wherein the method comprises:

expanding the unexpanded substantially in-contact portions of the inner surface of the wall of the expandable member such that the substantially variable thickness of the wall from the fixed portion to the variable portion thereof expands in the blood vessel at the interventional procedure site.

22. The method of claim 21, wherein the expandable member wall includes a portion adapted to be fixed and a portion adapted to be generally freely expandable, and the expansion enabling means are further adapted to enable the expandable member wall to be relatively stiff proximate the fixed portion thereof and relatively flexible proximate the expandable portion thereof, and expanding further comprises relatively stiffly expanding the wall of the expandable balloon proximate the fixed portion thereof and relatively flexibly expanding the wall of the expandable balloon proximate the expandable portion thereof.

23. The method of claim 21, wherein the substantially variable thickness of the wall is adapted to be substantially incrementally variable, and expanding further comprises expanding the substantially incrementally variable wall thickness of the expandable member.

24. The method of claim 21, wherein the substantially variable thickness of the wall is adapted to be thicker towards the fixed portion thereof, and expanding further comprises expanding the thicker wall portion of the expandable member.

25. The method of claim 21, wherein the substantially variable thickness of the wall is adapted to be substantially thick towards the fixed portion thereof, and expanding further comprises expanding the substantially thicker wall portion of the expandable member.

26. The method of claim 21, wherein the substantially variable thickness of the wall is adapted to be generally thin towards the expandable portion thereof, and expanding further comprises expanding the substantially thinner wall portion of the expandable member.

* * * * *